United States Patent [19]
Bhadra et al.

[11] Patent Number: 5,899,933
[45] Date of Patent: May 4, 1999

[54] NERVE CUFF ELECTRODE CARRIER

[75] Inventors: Narendra Bhadra, Cleveland Heights; J. Thomas Mortimer, Chagrin Falls, both of Ohio

[73] Assignee: Axon Engineering, Inc., Willoughby, Ohio

[21] Appl. No.: 08/876,790

[22] Filed: Jun. 16, 1997

[51] Int. Cl.⁶ ..................................................... A61N 1/05
[52] U.S. Cl. .......................................... 607/118; 607/377
[58] Field of Search .................................. 607/117, 118; 600/377, 393

[56] References Cited

U.S. PATENT DOCUMENTS 3,405,715  10/1968  Hagfors .................................... 607/118
5,344,438   9/1994  Testerman et al. ...................... 607/118

FOREIGN PATENT DOCUMENTS 1052236  11/1983  U.S.S.R. ................................. 607/118
91/17791  11/1991  WIPO .................................... 607/118

OTHER PUBLICATIONS

Paul Koole, Jan Holsheimer, Johannes J. Struijk, and Anton J. Verloop, Recruitment Characteristics of Nerve Fascicles Stimulated by a Multigroove Electrode, IEEE Transactions on Rehabilitation Engineering vol. 5. No. 1. Mar. 1997. pp. 40–50.

G. S. Brindley, An Implant To Empty The Bladder Or Close The Urethra, Journal of Neurology, Neurosurgery, and Psychiatry, 1997, 40, pp. 358–369.

G.S. Brindley, C.E. Polkey, D.N. Rushton, and L. Cardozo, Sacral Anterior Root Stimulators For Bladder control in Paraplegia: The First 50 Cases, ournal of Neurology, Neurosurgery, and Psychiatry,1986:40: pp. 1104–1114.

*Primary Examiner*—Lee Cohen
*Attorney, Agent, or Firm*—Jerrold J. Litzinger

[57] ABSTRACT

A device for coupling nerve cuff electrodes for stimulating nerves to a signal source for applying electrical signals for activation. The device comprises a carrier plate composed of a non-conductive material which contains a series of grooves for receiving selected nerve trunks. On either side of each groove is located a slot along the length of the groove, and a plurality of contacts are embedded within each groove. The contacts are releasably coupled to a power source which supplies a stimulating signal to the nerves. A spiral cuff electrode is wrapped through the slots to secure the nerve within the contact and provide for electrical conduction.

15 Claims, 5 Drawing Sheets

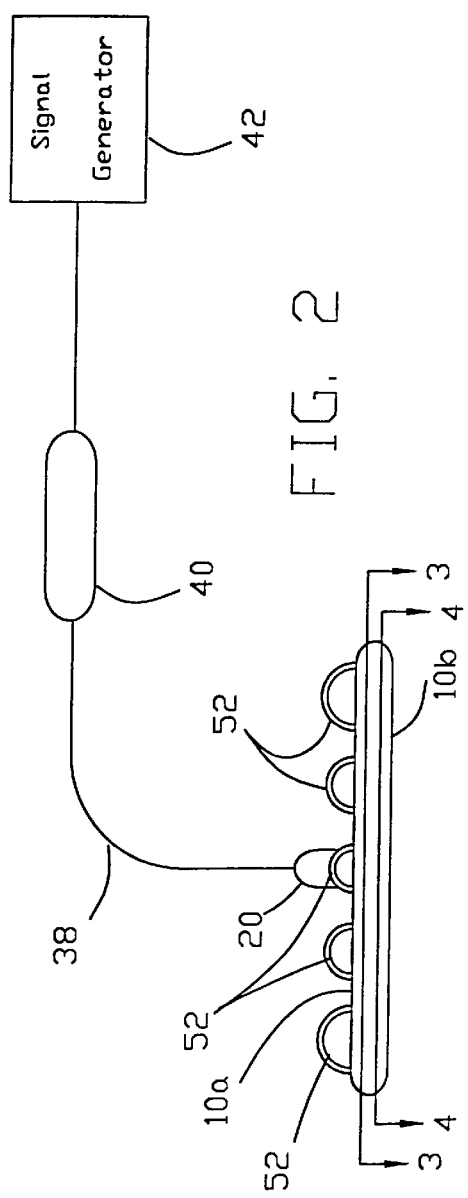
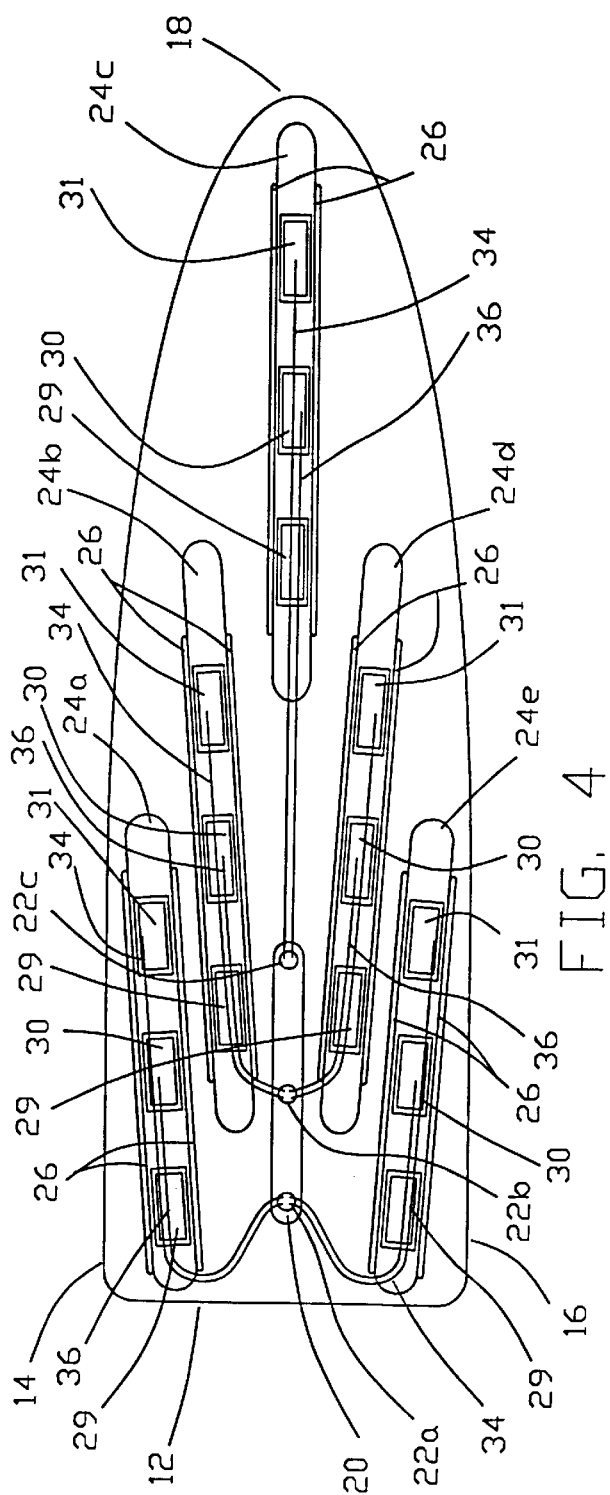

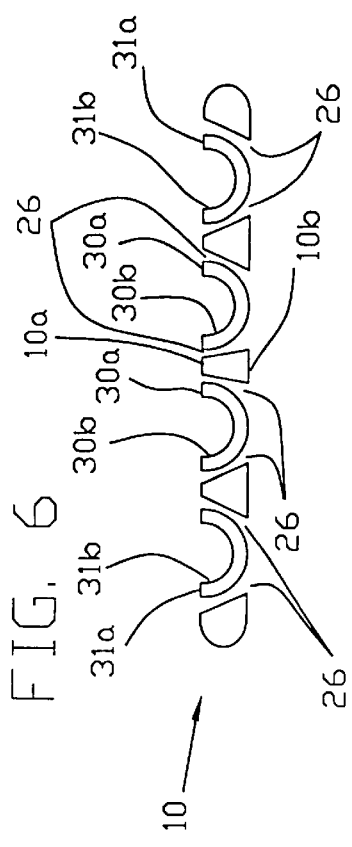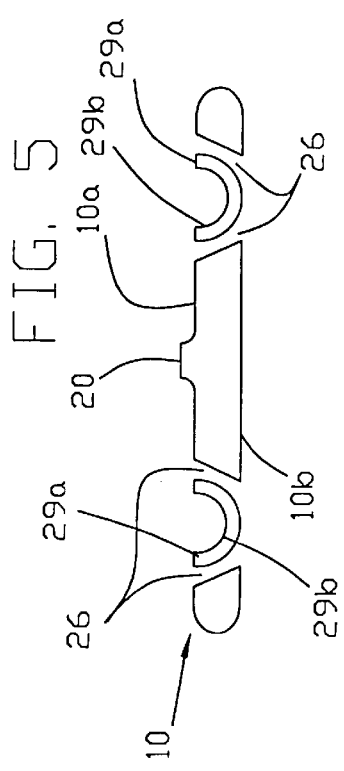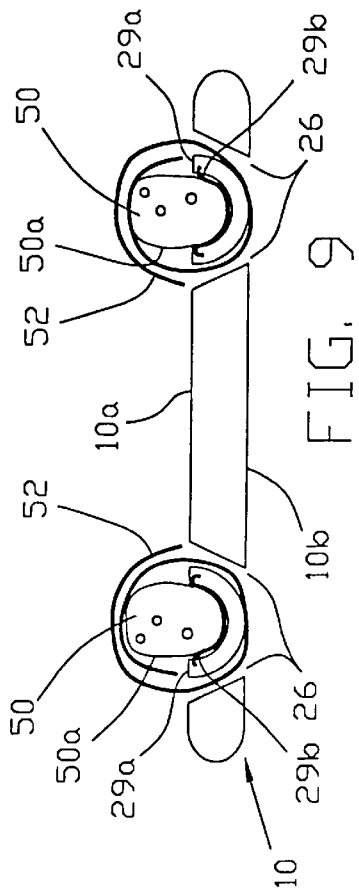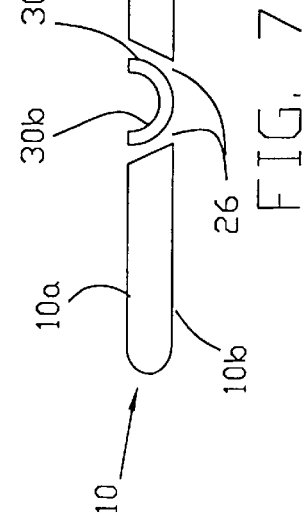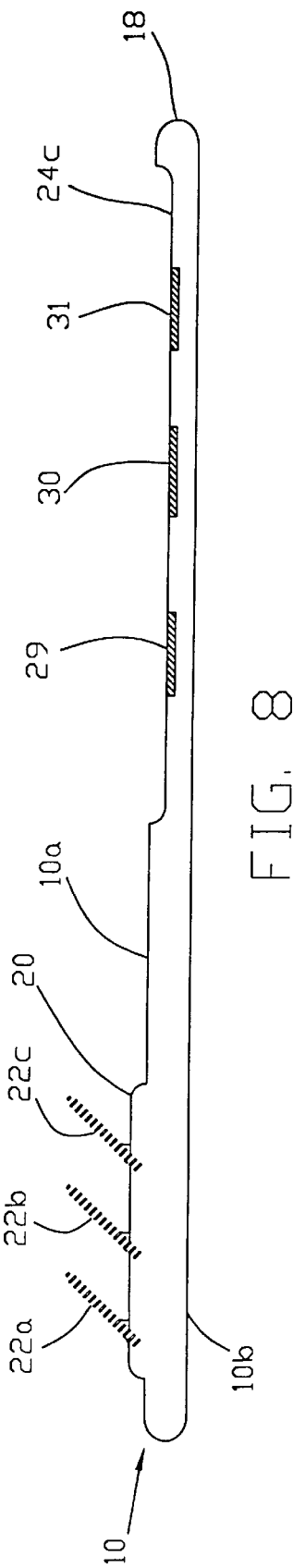

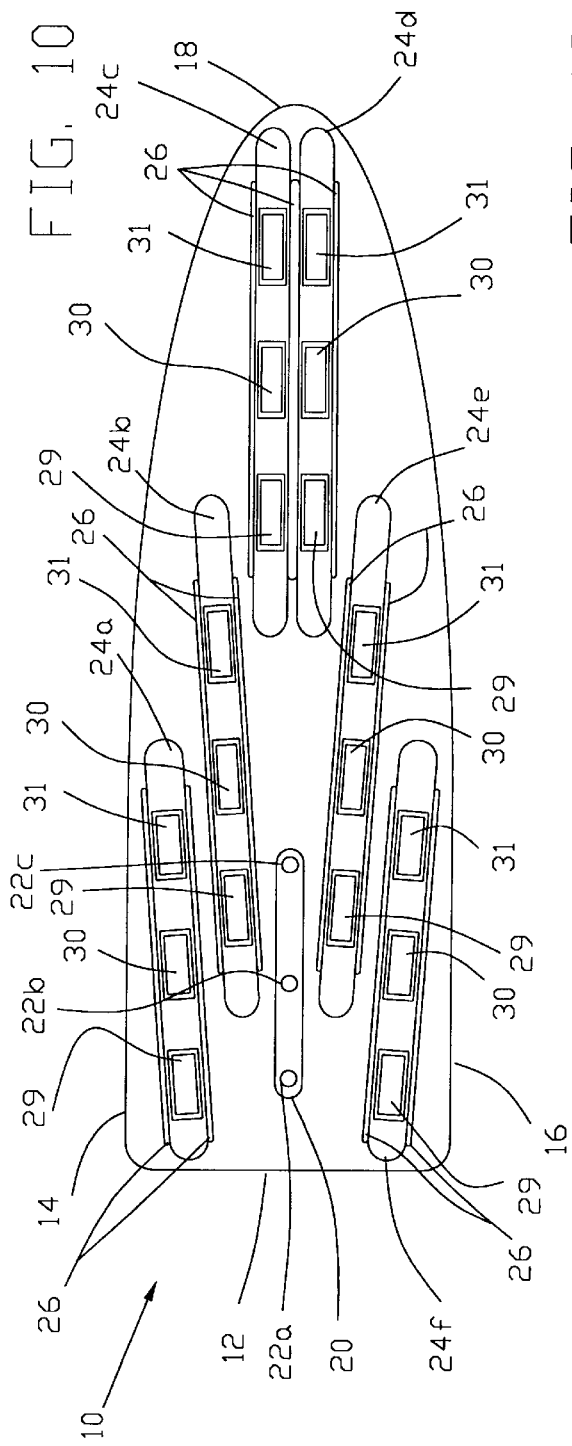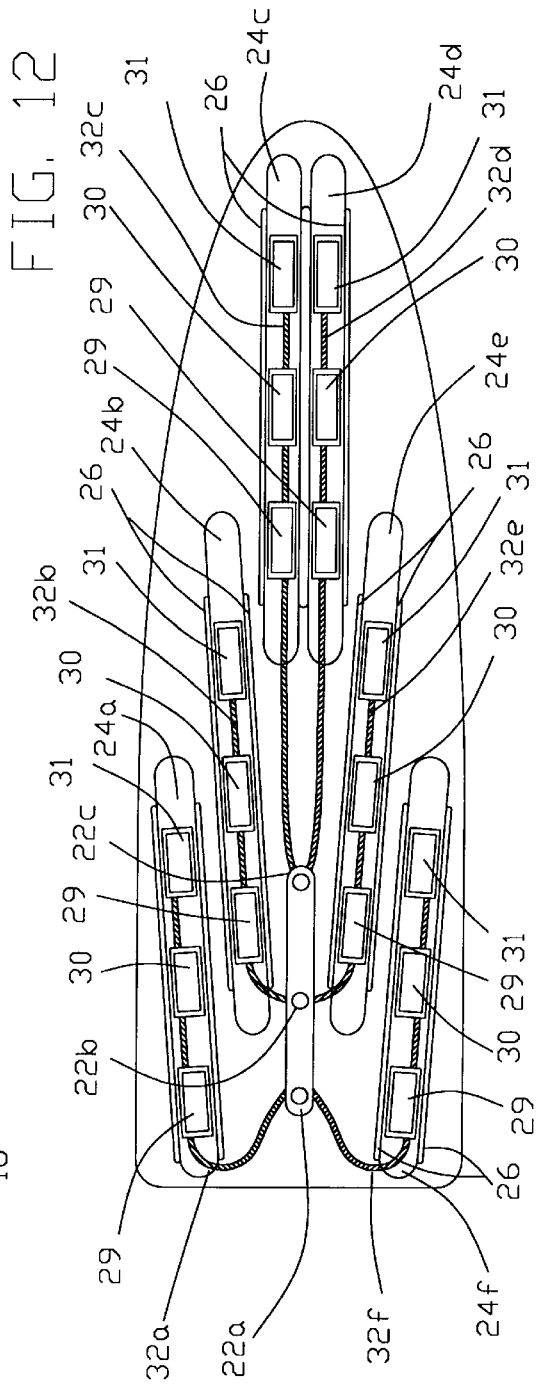

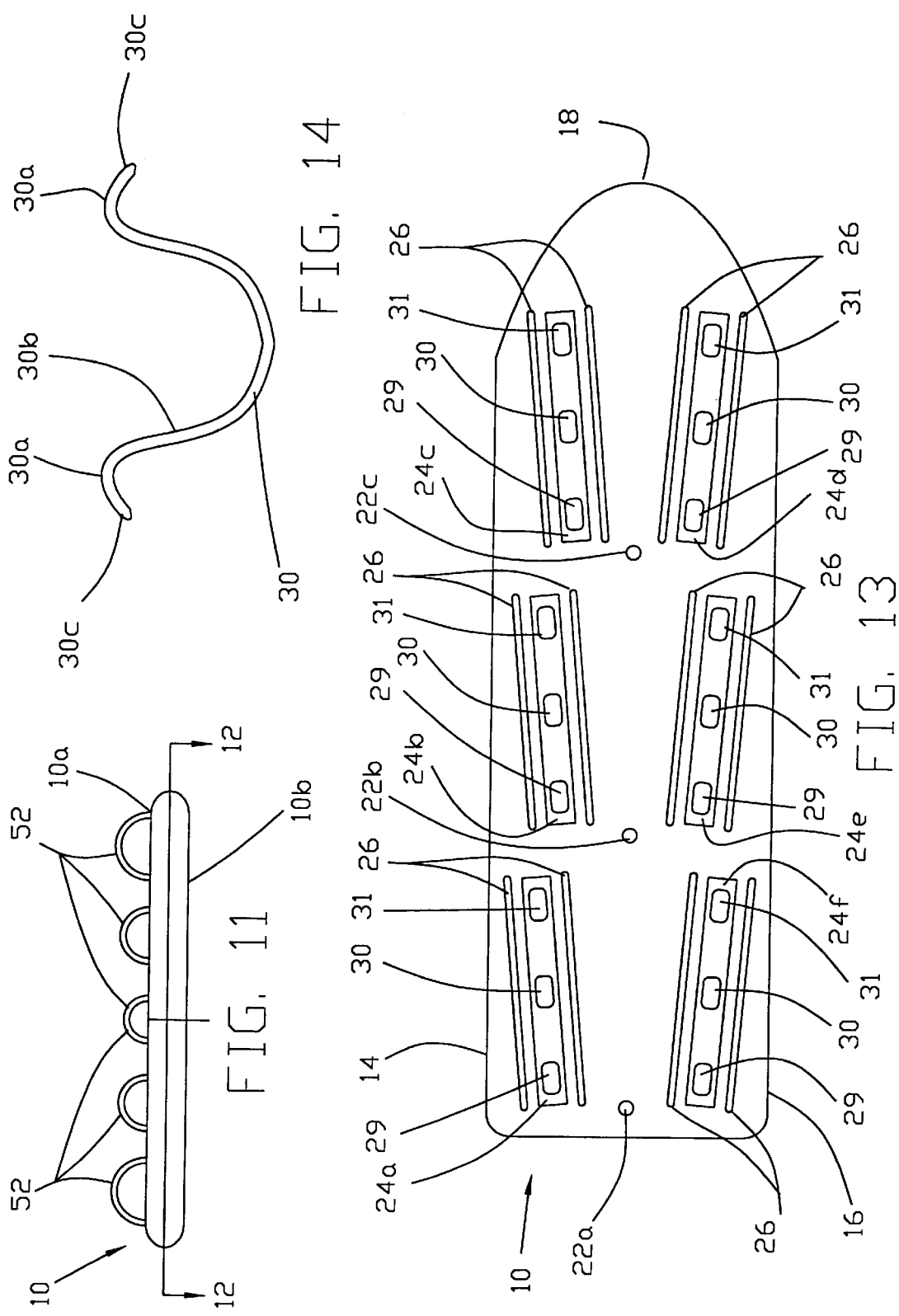

NERVE CUFF ELECTRODE CARRIER

BACKGROUND OF THE INVENTION

1. Field of the Invention

The present invention relates generally to the biomedical arts, and, in particular, to a device for use in conjunction with cuff electrodes for stimulating nerves.

2. Description of the Related Art

Functional electrical stimulation of the nervous system has been shown in recent years to offer great hope in restoring some degree of lost sensory and motor function in individuals with severe spinal cord injuries. Ways in which functional electrical stimulation of peripheral nerves can be utilized to restore a particular function include: (1) the use of surface electrodes to activate the nerves in the general region of interest; (2) the use of intramuscular electrodes, also to activate the nerves in a general region; and (3) the use of nerve cuff electrodes placed about specific nerves of interest and used to activate them specifically. The third alternative offers advantages over the first two in that it requires the least amount of stimulating current and hence charge injected into the tissue. In addition, it allows easy excitation of entire muscles rather than parts of muscles, a common situation for the first two categories. Because the use of nerve cuff electrodes requires delicate surgery, they are usually contemplated only when: (1) excitation of specific isolated muscles is desired; or (2) the generation of unidirectional action potentials is required.

Various prior art cuff electrodes have been utilized in the past to apply electrical stimuli to nerves. U.S. Pat. No. 4,602,624 is directed to a cuff electrode which encircles a nerve trunk with at least one electrical energy conductive member held against the tissue and a non-conductive sleeve extending to either side of the conductive member. This cuff is a self-curling sheet which is biased to curl into a light overlapping cylindrical spiral around the nerve trunk. U.S. Pat. No. 5,324,322 is directed to a cuff electrode having a spiral cuff portion which is connected to a spiral lead portion. The spiral cuff portion is coiled around a nerve, while the spiral lead portion is used to couple the device to an appropriate power source. U.S. Pat. No. 5,505,201 is directed to a helical nerve cuff electrode which curls into a helical spiral around a nerve fiber as it is ejected from a carrier tool.

While these spiral cuff electrodes are very effective in delivering the desired electrical pulses to selected nerves, they all suffer from some deficiency. The manner in which these electrodes are coupled to the power sources often makes the installation of these electrodes a difficult and very delicate procedure. Lead wires which attach the cuff electrodes to the power source must be bonded to each electrode by welding, soldering or using special conductive epoxies. These connections are often very difficult and labor intensive to make, requiring the time and talent of a skilled fabricator, and increase the physical size of the electrodes. In addition, these connections are subject to mechanical failure due to repeated flexure of the electrodes, and any failure at the connection of the electrode and lead requires removal of the electrode and the implantation of a new electrode.

Finally, the conductor leads themselves must travel from the electrodes to the power source. These leads must often be anchored by a strain relief to protect the connections from physical movement. Also, if there are several electrodes to be implanted in the same area of the body, the number of leads required to connect the power source to the electrodes will contribute significantly to the overall size of the implanted system, making installation more difficult.

The present invention provides a new and improved nerve cuff electrode carrier which overcomes the above referenced problems and others.

SUMMARY OF THE INVENTION

It is, therefore, an object of the present invention to provide a device which provides for the coupling of a plurality of nerve cuff electrodes to a removable conductor lead group.

It is also an object of the present invention to provide a device which can accommodate and position a plurality of nerve cuff electrodes in a simpler and safer manner than previously possible.

It is a further object of the present invention to provide a device which simplifies the installation of nerve cuff electrodes within the human lumbosacral spinal canal.

Still further advantages of the present invention will become apparent to those of ordinary skill in the art upon reading and understanding the following detailed description of the preferred embodiment.

BRIEF DESCRIPTION OF THE DRAWINGS

FIG. 1 is a top elevational view of a nerve cuff electrode carrier in accordance with a preferred embodiment of the present invention;

FIG. 2 is a side elevational view of the carrier of FIG. 1, additionally showing the external lead arrangement;

FIG. 3 is a cross-sectional view taken along lines 3—3 of FIG. 2;

FIG. 4 is a cross-sectional view taken along lines 4—4 of FIG. 2;

FIG. 5 is a cross-sectional view taken along lines 5—5 of FIG. 1;

FIG. 6 is a cross-sectional view taken along lines 6—6 of FIG. 1;

FIG. 7 is a cross-sectional view taken along lines 7—7 of FIG. 1;

FIG. 8 is a cross-sectional view taken along lines 8—8 of FIG. 1;

FIG. 9 is an enlarged cross-sectional view similar to FIG. 5 showing electrodes in position on the carrier of the present invention;

FIG. 10 is a top elevational view of a second embodiment of the present invention;

FIG. 11 is a side elevational view of the carrier of FIG. 10;

FIG. 12 is a cross-sectional view taken along lines 12—12 of FIG. 11;

FIG. 13 is a top elevational view of a modified version of the carrier device as shown in FIG. 10; and FIG. 14 is a cross-sectional view of an alternate contact that may be used in the present invention.

DETAILED DESCRIPTION OF THE PREFERRED EMBODIMENT

Figures 1, 3:
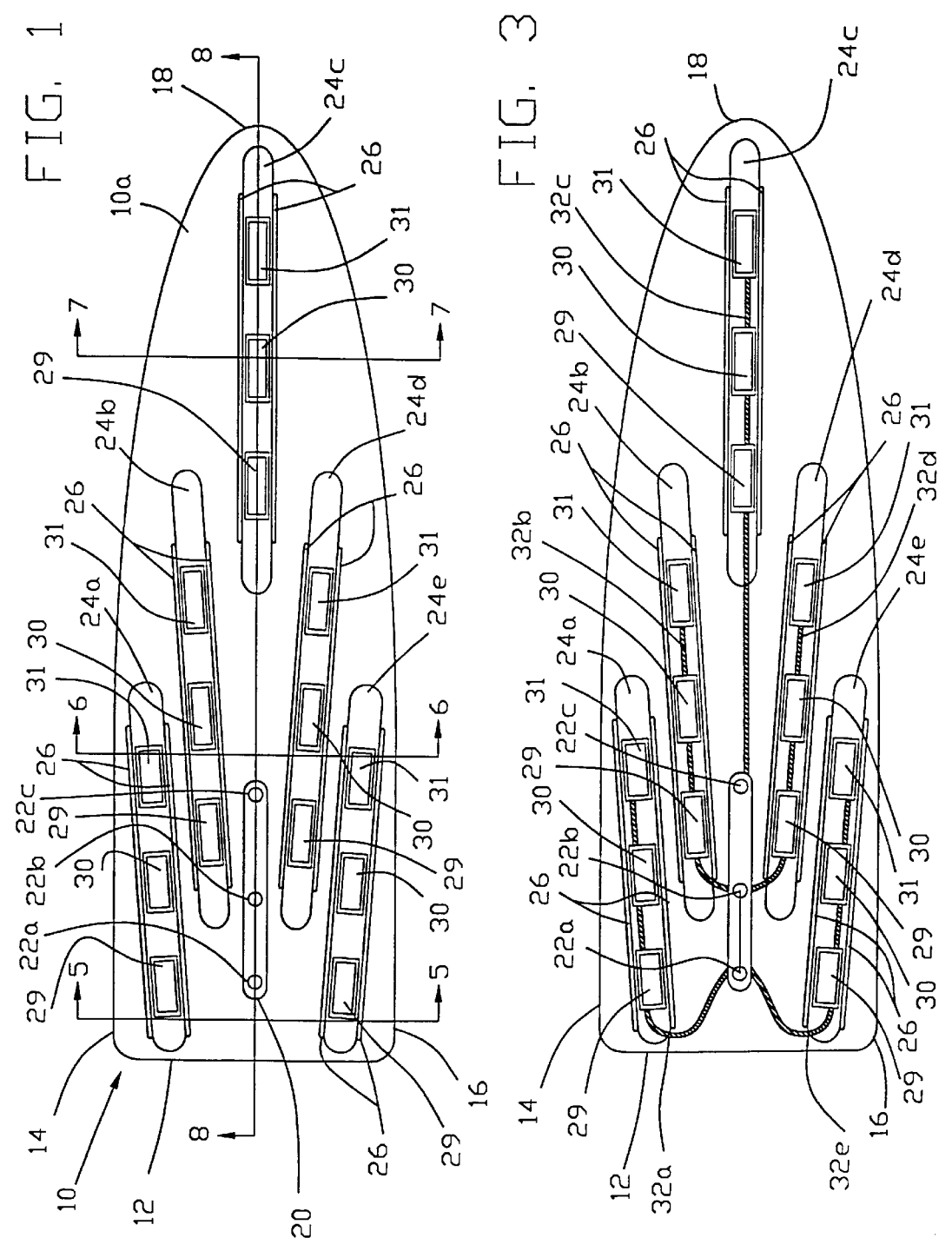

Referring more particularly to the drawings there is shown therein a carrier device or plate, generally indicated at 10, which embodies the principles of the present invention. In the present embodiment, carrier plate 10, which has an upper surface 10a and a lower surface 10b, comprises a planar device having a proximal end 12, and a pair of essentially parallel sides 14, 16 which converge to form a rounded distal end 18. Carrier 10 is preferably composed of silicone rubber molded into the shape shown in FIG. 1, although other materials and shapes could be successfully used for the device. Carrier 10 may also be fabricated from two layers of silicone rubber which are bonded together with a heat curing silicone elastomer or any suitable adhesive.

A raised section 20 of carrier 10 is located in the central region near proximal end 12. Section 20 contains a plurality of apertures 22a–c which are formed upon upper surface 10a. Upper surface 10a also includes a plurality of grooves or channels 24a–e, each of which extends linearly from proximal end 12 toward distal end 18 aligned adjacent one another from side 14 toward side 16. Finally, on either side of each channel 24, a through slot 26 is located. Slots 26, which are situated parallel to each channel 24 and positioned on either side, extend completely through carrier 10 from upper surface 10a to lower surface 10b. Channels 24 may be angled in orientation, as can be seen in FIGS. 1 and 10, in order to comfortably accommodate the spinal nerves in their anatomical configuration.

Molded into carrier 10 within channels 24 are a plurality of electrically conductive contacts. In the present embodiment, the contacts are arranged such that three contacts 29, 30, and 31 are located within each channel 24. Using contact 30 as an example, each contact has a hollow hemicylindrical shape having a top surface 30a and a curved surface 30b and is preferably constructed from platinum, although the contacts could be constructed from iridium, stainless steel, or any other metal having similar properties. The contacts are molded within the body of carrier 10 such that top surfaces 29a, 30a, 31a of contacts 29, 30, 31 respectively are substantially flush with the upper surface 10a of carrier 10, as can be most clearly seen in FIGS. 5, 6, and 7. The contacts are preferably sized such that a nerve trunk can be physically accommodated by curved surface 29b, 30b, 31b of contact 29, 30, 31 respectively. In order to add to the holding power of the contacts within the molded carrier plate 10, it may be advisable to use contacts which are shaped similar to the contact shown in FIG. 14. Contact 30 shown in FIG. 14 contains curved sections 30c which enable the contact to embed more securely within carrier 10 for greater reliability of the device.

Referring now to FIG. 3, it can be seen that each of contacts 29, 30, 31 within a single channel 24 are coupled together by a conductor 32. Each of conductors 32a–e is molded within carrier 10, connecting each of contacts 29, 30, 31 related to a particular channel 24 to provide a stronger and more reliable connection, and then continues through one of apertures 22a–c molded within section 20 of carrier 10.

The actual internal connections of the contacts of the present embodiment can best be seen in FIG. 4. Referring now to FIG. 4, separate leads 34 and 36, within each conductor 32 are shown. For each of the channels 24, a lead 34 is physically attached, by welding or a similar process, to the proximal contact 29 and the distal contact 31 which act as anodes while the center contact 30 of the channel, which acts as a cathode, is attached to the second lead 36. Leads 34 and 36 within conductor 32 from each channel 24 pass through apertures 22 within section 20 of carrier 10 to form a conductor bundle 38 which is connected to an in-line connector 40 shown in FIG. 2. Connector 40 provides a convenient and easily removable coupling system to a power source 42 which is used to provide the appropriate electrical signals to the nerve cuff electrodes to provide functional electrical stimulation of the nervous system.

Having described the elements of the carrier device of the present invention, the installation of the preferred embodiment of carrier 10 will now be described. In the present embodiment, carrier 10 is designed to be positioned intradurally in the spinal area at approximately the 4th or 5th lumbar vertebrae. The physical size of carrier 10 is approximately 40 mm in length and approximately 12 mm in width, and having a depth of approximately 1 mm. The contacts within channel 24 are sized to deliver the required current for stimulation without adversely affecting the metallic contact itself, thus preventing corrosion or formation of any potentially biologically harmful oxidation products. Spacing between the contacts is ideally determined by the diameter of the largest size nerve fibers to be stimulated, such that, in the desired procedure, at least two nodes of the uniform distribution of nerve fibers lie between contacts for the selected activation.

Referring now to FIG. 9, a selected nerve trunk 50 is positioned within one of channels 24 within carrier 10 such that its outer surface 50a is in contact with the inner curved surface 29b of each of the contacts within the selected channel. A spiral cuff electrode 52, which is similar in construction to that taught in U.S. Pat. Nos. 4,602,624 and 5,505,201 in that it is a self curling electrode which provides regions of electrical conduction in contact with the nerve and can be delivered to the installation site in a flattened state, is positioned at the selected channel 24. As cuff electrode 52 is permitted to curl, it is guided through slots 26 positioned on either side of channel 24 such that electrode 52 positions nerve trunk 50 in physical contact with inner surface 29b of contact 29 and constantly urges nerve trunk 50 into that position with the contact by virtue of the cuff electrode design.

After the desired nerve cuff electrodes have been installed on the carrier, it is now possible to introduce electrical signals to the nerve trunk. A power source 42 is coupled to cuff electrodes 52 through connector 40. In the present embodiment, power source 42 generates an electric pulse train which is taught in U.S. Pat. No. 4,608,985 to cuff electrodes 52 and contacts 29, 30, 31 to accomplish the desired electrical stimulation of the nervous system of a patient.

FIGS. 10–12 show a second preferred embodiment of the present invention; and like parts have been given like index numerals. In this embodiment, however, an additional channel 24f is present within carrier device 10, such that it is possible to stimulate nerves in six separate compartments using this device.

FIG. 13 illustrates a modified version of the carrier device shown in FIGS. 10–12 with all of channels 24a–f angled with respect to the central axis of carrier 10. In addition, apertures 22a–c are spaced at greater intervals along the length of device 10 rather than on a raised section of the device, as is shown in FIG. 1.

As use herein and in the claims, such words as "distal", "proximal", "top", "bottom", and the like are used in conjunction with the drawings for purposes of clarity. It will be appreciated that carrier device 10, in use, may be mounted in any appropriate orientation.

While the invention has been shown and described in terms of several embodiments thereof, it will be understood that this invention is not limited to these particular embodiments and that many changes and modifications may be made without departing from the true spirit and scope of the invention as defined in the appended claims.

What is claimed is:

1. A device for coupling spiral cuff electrodes to nerves for applying electrical signals from a signal generator to a nerve trunk to stimulate a nerve in a mammal, comprising:

a carrier plate, formed from a non-conductive material, having a plurality of grooves formed therein, with each groove capable of accommodating at least one nerve trunk, said plate having a pair of through slots associated with each groove wherein said groove is positioned between said slots;

a plurality of electrically conductive contacts, each having a hollow hemicylindical outer surface, located within each groove;

and an electrical conductor, located within said carrier plate, associated with each groove, for coupling said contacts to a signal generator;

such that when a nerve trunk is positioned within a groove of said carrier plate in physical contact with the outer surface of said contacts and a spiral cuff electrode is positioned within said slots of said carrier plate encircling said nerve trunk and in physical contact with the nerve trunk, electrical signals from a signal generator may be applied through said electrical conductor and said contacts to the nerve trunk to stimulate the nerve.

2. The device of claim 1, wherein said plate is formed from molded silicone rubber.

3. The device of claim 1, wherein said contacts are constructed from platinum.

4. The device of claim 1, wherein said contacts are constructed from iridium.

5. The device of claim 1, wherein said plurality of contacts consists of three contacts within each groove.

6. The device of claim 5, wherein at least one contact acts as an anode and at least one contact acts as a cathode.

7. The device of claim 5, wherein two of said contacts are electrically coupled together.

8. The device of claim 1, wherein each conductor consists of two separate leads.

9. The device of claim 1, wherein said electrical conductor is adapted to be releasably coupled to said signal generator.

10. The device of claim 1, wherein the maximum number of grooves contained in said plate is six.

11. A device for coupling a spiral cuff electrode to a nerve for applying electrical signals for a signal generator to stimulate a nerve trunk of a mammal, comprising:

a carrier plate, formed from a non-conductive material, having at least one groove formed therein capable of receiving a nerve trunk, said plate having a through slot located adjacent each side of said groove;

at least one electrically conductive contact located within said groove, said contact having a hollow hemicylindrical upper surface;

and means for electrically coupling said contact to a signal generator;

such that, when a nerve trunk is positioned within said groove in physical contact with said contact and a spiral cuff electrode is coupled to said carrier plate through said slots encircling and in physical contact with the nerve trunk, electrical signals from a signal generator may be applied through said electrical coupling means and said contact to stimulate the nerve trunk.

12. The device of claim 11, wherein said electrical coupling means is adapted to be coupled to said signal generator through an in-line connector.

13. The device of claim 11, wherein said contact is constructed from platinum.

14. The device of claim 11, wherein said contact is constructed from iridium.

15. The device of claim 11, wherein said plate is formed from silicone rubber.

* * * * *